US 8,227,465 B2

United States Patent
Moinet et al.

(10) Patent No.: US 8,227,465 B2
(45) Date of Patent: Jul. 24, 2012

(54) COMBINATION OF TRIAZINE DERIVATIVES AND INSULIN SECRETION STIMULATORS

(75) Inventors: Gérard Moinet, Orsay (FR); Daniel Cravo, Montesson (FR); Didier Mesangeau, Combs-la-Ville (FR)

(73) Assignee: Poxel SAS, Lyons (FR)

( * ) Notice: Subject to any disclaimer, the term of this patent is extended or adjusted under 35 U.S.C. 154(b) by 267 days.

(21) Appl. No.: 12/160,637

(22) PCT Filed: Dec. 18, 2006

(86) PCT No.: PCT/EP2006/012182
§ 371 (c)(1),
(2), (4) Date: Jul. 11, 2008

(87) PCT Pub. No.: WO2007/079914
PCT Pub. Date: Jul. 19, 2007

(65) Prior Publication Data
US 2010/0233255 A1    Sep. 16, 2010

(30) Foreign Application Priority Data
Jan. 13, 2006  (FR) ....................... 06 00342

(51) Int. Cl.
*C07D 251/48* (2006.01)
(52) U.S. Cl. ........ 514/245; 514/241; 514/183; 544/209; 544/208; 544/204; 544/194; 544/180
(58) Field of Classification Search ........... None
See application file for complete search history.

(56) References Cited

U.S. PATENT DOCUMENTS

| 6,559,188 | B1 * | 5/2003 | Gatlin et al. ............ 514/641 |
| 2002/0183345 | A1 | 12/2002 | Piper |
| 2003/0109530 | A1 | 6/2003 | Moinet et al. |
| 2003/0139434 | A1 * | 7/2003 | Balkan et al. ............ 514/275 |
| 2004/0096499 | A1 | 5/2004 | Vaya et al. |
| 2004/0127414 | A1 * | 7/2004 | Yakubu-Madus et al. ...... 514/12 |
| 2004/0147564 | A1 * | 7/2004 | Rao et al. .............. 514/342 |
| 2005/0239887 | A1 | 10/2005 | Ochoa |
| 2006/0024365 | A1 | 2/2006 | Vaya et al. |
| 2006/0153916 | A1 | 7/2006 | Vaya et al. |
| 2006/0223803 | A1 | 10/2006 | Moinet et al. |

FOREIGN PATENT DOCUMENTS

| WO | WO 01/55122 A1 | 8/2001 |
| WO | WO 2004/012700 A2 | 2/2004 |
| WO | WO 2004/089917 A2 | 10/2004 |
| WO | WO 2005020983 A2 * | 3/2005 |

OTHER PUBLICATIONS

"Oral combination therapy for type 2 diabetes" by Charpentier, Diab./Metab. Res. Rev. 18, S70-76 (2002).*
"The role of oral antidiabetic agents: why and when to use an early-phase insulin secretion agent in Type 2 diabetes mellitus" by Standl et al., Diobetologia 46 (Suppl. 1), M30-36 (2003).*

* cited by examiner

*Primary Examiner* — Brandon Fetterolf
*Assistant Examiner* — Theodore R West
(74) *Attorney, Agent, or Firm* — Saliwanchik, Lloyd & Eisenschenk

(57) ABSTRACT

The present patent application relates to novel combinations of a triazine derivative and of an insulin secretion stimulator.

26 Claims, No Drawings

COMBINATION OF TRIAZINE DERIVATIVES AND INSULIN SECRETION STIMULATORS

FIELD OF THE INVENTION

The present invention relates to a pharmaceutical composition of triazine derivatives or described pharmaceutically acceptable salts thereof with an insulin secretion stimulator, for the manufacture of a medicament that can be used in the treatment of non-insulin-dependent diabetes and pathologies associated with insulin resistance syndrome.

TECHNICAL BACKGROUND

"Diabetes mellitus" (or diabetes) is one of the most prevalent diseases in the world today. Individuals suffering from diabetes have been divided into two classes, namely type I or insulin-dependent diabetes mellitus and type II or non-insulin-dependent diabetes mellitus (NIDDM). Non-insulin-dependent diabetes mellitus (NIDDM) accounts for approximately 90% of all diabetics, and is estimated to affect 12 to 14 million adults in the United States alone (6.6% of the population). NIDDM is characterised both by fasting hyperglycaemia and exaggerated postprandial increases in plasmatic glucose levels. NIDDM is associated with a variety of long-term complications, including microvascular diseases, such as retinopathy, nephropathy and neuropathy, and macrovascular diseases, such as coronary heart disease. Numerous studies in animal models show a causal relationship between long-term complications and hyperglycaemia. Recent results obtained by the Diabetes Control and Complications Trial (DCCT) and the Stockholm Prospective Study have for the first time demonstrated this relationship in man by showing that insulin-dependent diabetics have a substantially lower risk of development and progression of these complications if they are subjected to tighter glycaemic control. Tighter control is also expected to benefit NIDDM patients.

Hyperglycaemia in the case of NIDDM is associated with two biochemical anomalies, namely insulin resistance and insufficiency of insulin secretion.

The initial treatment of NIDDM is based on a controlled diet and controlled physical exercise, since a considerable number of diabetics are overweight or obese (~67%) and since loss of weight can improve insulin secretion and sensitivity to insulin and lead to normal glycaemia.

Patients suffering from hyperglycaemia that cannot be controlled solely by diet and/or physical exercise are then treated with oral antidiabetics.

Several categories of oral antidiabetics are currently used in monotherapy for the treatment of NIDDM:
  insulin secretion stimulators. They are represented, firstly, by sulfonylureas (SU) and by "glinides". As regards SUs, mention will be made in particular of carbutamide (Glucidoral®), glibenclamide/glyburide (Daonil®, Euglucan®), glibomuride (Glutril®), gliclazide (Diamicron®), glimepiride (Amarel®) and glipizide (Glibenese®). As regards the "glinides", mention will be made in particular of repaglinide (NovoNorm®);
  agents that reduce glucogenesis, represented by the biguanides. Mention will be made in particular of metformin (Glucophage®, Stagid®);
  insulin sensitisers, represented mainly by thiazolidinediones (TZD). Mention will be made in particular of pioglitazone (Actos®) and rosiglitazone (Avandia®);
  alpha-glucosidase inhibitors. Mention will be made in particular of acarbose (Glucor®) and miglitol (Diastabol®).

However, the monotherapy may show a loss of efficacy over time. This is referred to as "secondary deficiency". This may represent up to 50% unsatisfactory response after 10 years of treatment. The studies conducted have shown that it is possible to deal with this problem by combining in the same pharmaceutical form metformin with sulfonylureas or TZD (EP 869 796 B1, EP 974 365 B1, EP 861 666 B1, WO 03/006004 A2), and a number of these fixed combinations have been marketed:
  metformin+glibenclamide/glyburide (Glucovance®)
  metformin+glipizide (Metaglip®)
  metformin+rosiglitazone (Avandamet®).

Triazine derivatives with an antidiabetic effect comparable to that of metformin have been described in WO 01/55122.

The applicant has demonstrated, entirely unexpectedly, that the combination of an antidiabetic agent of triazine type, such as those described in WO 01/55122, and of an insulin secretion stimulator shows a synergistic effect and a very strong decrease in side effects compared with metformin combinations, especially as regards nausea and diarrhea.

DESCRIPTION OF THE INVENTION

The present invention thus relates to a novel pharmaceutical composition comprising an antidiabetic agent of triazine type (WO 01/55122) and an insulin secretion stimulator with one or more pharmaceutically acceptable excipients.

The triazine derivative is preferably represented by the general formula (I):

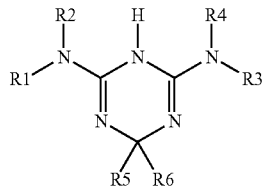

in which:
R1, R2, R3 and R4 are independently chosen from the following groups:
  —H,
  —(C1-C20)alkyl optionally substituted by halogen, (C1-C5)alkyl, (C1-C5)alkoxy or (C3-C8)cycloalkyl,
  —(C2-C20)alkenyl optionally substituted by halogen, (C1-C5)alkyl or (C1-C5)alkoxy
  —(C2-C20)alkynyl optionally substituted by halogen, (C1-C5)alkyl or (C1-C5)alkoxy
  —(C3-C8)cycloalkyl optionally substituted by (C1-C5)alkyl or (C1-C5)alkoxy
  -hetero(C3-C8)cycloalkyl bearing one or more heteroatoms chosen from N, O and S and optionally substituted by (C1-C5)alkyl or (C1-C5)-alkoxy
  —(C6-C14)aryl(C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
  —(C6-C14)aryl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
  —(C1-C13)heteroaryl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R1 and R2, on the one hand, and R3 and R4, on the other hand, is possibly forming with the nitrogen atom an n-membered ring (n between 3 and 8) optionally containing one or more heteroatoms chosen from N, O and S and possibly being substituted by one or more of the following groups: amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl-(C1-C5)alkoxy, cyano, trifluoromethyl, carboxyl, carboxymethyl or carboxyethyl, R5 and R6 are independently chosen from the following groups:
—H,
—(C1-C20)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
—(C2-C20)alkenyl optionally substituted by amino, hydroxyl, thio, halogen, (C1-C5)alkyl, (C1-C5)alkoxy, (C1-C5)alkylthio, (C1-C5)alkyl-amino, (C6-C14)aryloxy, (C6-C14)aryl(C1-C5)alkoxy, cyano, trifluoro-methyl, carboxyl, carboxymethyl or carboxyethyl,
—(C2-C20)alkynyl optionally substituted by amino, hydroxyl, thio, halogen, (C1-C5)alkyl, (C1-C5)alkoxy, (C1-C5)alkylthio, (C1-C5)alkyl-amino, (C6-C14)aryloxy, (C6-C14)aryl(C1-C5)alkoxy, cyano, trifluoro-methyl, carboxyl, carboxymethyl or carboxyethyl,
—(C3-C8)cycloalkyl optionally substituted by amino, hydroxyl, thio, halogen, (C1-C5)alkyl, (C1-C5)alkoxy, (C1-C5)alkylthio, (C1-C5)alkyl-amino, (C6-C14)aryloxy, (C6-C14)aryl(C1-C5)alkoxy, cyano, trifluoro-methyl, carboxyl, carboxymethyl or carboxyethyl,
-hetero(C3-C8)cycloalkyl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
—(C6-C14)aryl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
—(C1-C13)heteroaryl bearing one or more heteroatoms chosen from N, O and S and optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
—(C6-C14)aryl(C1-C5)alkyl optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl,
—R5 and R6 possibly forming with the carbon atom to which they are attached an m-membered ring (m between 3 and 8) optionally containing one or more heteroatoms chosen from N, O and S and possibly being substituted by amino, hydroxyl, thio, halogen, (C1-C5)alkyl, (C1-C5)-alkoxy, (C1-C5)alkylthio, (C1-C5)alkylamino, (C6-C14)aryloxy, (C6-C14)-aryl(C1-C5)alkoxy, cyano, trifluoromethyl, carboxyl, carboxymethyl or carboxyethyl,
or possibly forming with the carbon atom a C10-C30 polycyclic residue optionally substituted by amino, hydroxyl, thio, halogen, (C1-C5)alkyl, (C1-C5)alkoxy, (C1-C5)alkylthio, (C1-C5)alkylamino, (C6-C14)aryloxy, (C6-C14)aryl(C1-C5)alkoxy, cyano, trifluoromethyl, carboxyl, carboxymethyl or carboxyethyl, R5 and R6 together also possibly representing the group =O or =S, the nitrogen atom of a heterocycloalkyl or heteroaryl group possibly being substituted by a (C1-C5)alkyl, (C3-C8)cycloalkyl, (C6-C14)aryl, (C6-C14)-aryl(C1-C5)alkyl or (C1-C6)acyl group, and also the racemic forms, tautomers, enantiomers, diastereoisomers, epimers and mixtures thereof, and the pharmaceutically acceptable salts.

The term "m-membered ring formed by R5 and R6" in particular means a saturated ring, such as a cyclohexyl, piperidyl or tetrahydro-pyranyl group.

The term "polycyclic group formed by R5 and R6" means an optionally substituted carbon-based polycyclic group and in particular a steroid residue.

One particular group of the invention concerns the pharmaceutical compositions according to the invention in which the triazine derivatives are compounds of the formula (I) in which R5 is hydrogen.

Another particular group of the invention concerns the pharmaceutical compositions according to the invention in which the triazine derivatives are compounds of the formula (I) in which R5 and R6 form with the carbon atom to which they are attached an m-membered ring (m between 3 and 8) optionally containing one or more heteroatoms chosen from N, O and S and possibly being substituted by one or more of the following groups: (C1-C5)alkyl, amino, hydroxyl, (C1-C5)alkylamino, alkoxy(C1-C5), (C1-C5)alkylthio, (C6-C14)aryl, (C6-C14)aryl(C1-C5)alkoxy, or form with the carbon atom a C10-C30 polycyclic residue optionally substituted by amino, hydroxyl, thio, halogen, (C1-C5)alkyl, (C1-C5)-alkoxy, (C1-C5)alkylthio, (C1-C5)alkylamino, (C6-C14)aryloxy, (C6-C14)-aryl(C1-C5)alkoxy, cyano, trifluoromethyl, carboxyl, carboxymethyl or carboxyethyl.

Another particular group of the invention concerns the pharmaceutical compositions according to the invention in which the triazine derivatives are compounds of the formula (I) in which R5 and R6 are independently chosen from H and —(C1-C20)alkyl groups optionally substituted by amino, hydroxyl, thio, halogen, (C1-C5)alkyl, (C1-C5)alkoxy, (C1-C5)alkyl-thio, (C1-C5)alkylamino, (C6-C14)aryloxy, (C6-C14)aryl(C1-C5)alkoxy, cyano, trifluoromethyl, carboxyl, carboxymethyl or carboxyethyl.

Preferably, R1, R2, R3 and R4 are independently chosen from H and (C1-C20)alkyl groups optionally substituted by halogen, (C1-C5)alkyl, (C1-C5)alkoxy or (C3-C8)cycloalkyl; more preferably, R1=R2=H and R3=R4=(C1-C20)alkyl optionally substituted by halogen, (C1-C5)alkyl, (C1-C5)alkoxy, (C3-C8)cycloalkyl or vice versa.

Preferably, R5 and R6 are independently chosen from H and (C1-C20)alkyl groups optionally substituted by amino, hydroxyl, thio, halogen, (C1-C5)alkyl, (C1-C5)alkoxy, (C1-C5)alkylthio, (C1-C5)alkyl-amino, (C6-C14)aryloxy, (C6-C14)aryl(C1-C5)alkoxy, cyano, trifluoro-methyl, carboxyl, carboxymethyl or carboxyethyl; more preferably, R5=H and R6=(C1-C20)alkyl optionally substituted by amino, hydroxyl, thio, halogen, (C1-C5)alkyl, (C1-C5)alkoxy, (C1-C5)alkylthio, (C1-C5)alkyl-amino, (C6-C14)aryloxy, (C6-C14)aryl(C1-C5)alkoxy, cyano, trifluoro-methyl, carboxyl, carboxymethyl or carboxyethyl or vice versa.

A more particular group of the invention concerns the pharmaceutical compositions according to the invention in which the triazine derivatives are compounds of the formula (I) in which R1 and R2 are a methyl group and R3 and R4 represent a hydrogen.

Compounds of the formula (I) that may especially be mentioned include:

| | Formula | Salt |
|---|---|---|
| 1 | 2-amino-4-(dimethylamino)-6-ethyl-1,6-dihydro-1,3,5-triazine | HCl |
| 2 | 2,4-bis(dimethylamino)-6-methyl-1,6-dihydro-1,3,5-triazine | HCl |
| 3 | 2-amino-4-(dimethylamino)-6,6-dimethyl-1,6-dihydro-1,3,5-triazine | |
| 4 | 2-amino-4-(dimethylamino)-1,6-dihydro-6,6-spirocyclohexyl-1,3,5-triazine | HCl |
| 5 | 2-amino-4-(dimethylamino)-6,6-dimethyl-1,6-dihydro-1,3,5-triazine | Methanesulfonate |
| 6 | 2-amino-4-(dimethylamino)-6-methyl-6-(3-hydroxypropyl)-1,6-dihydro-1,3,5-triazine | |
| 7 | 2-amino-4-(dimethylamino)-6-methyl-6-(3-hydroxypropyl)-1,6-dihydro-1,3,5-triazine | HCl |

| | Formula | Salt |
|---|---|---|
| 8 | 6-(dimethylamino)-N-(prop-2-en-1-yl)-2,2-dimethyl-1,2-dihydro-1,3,5-triazin-4-amine | HCl |
| 9 | 6-(dimethylamino)-N-(propan-2-yl)-2,2-dimethyl-1,2-dihydro-1,3,5-triazin-4-amine | HCl |
| 10 | 4-amino-6-(dimethylamino)-2-phenyl-1,2-dihydro-1,3,5-triazine | HCl |
| 11 | 4-amino-6-(dimethylamino)-2-(4-methoxyphenyl)-1,2-dihydro-1,3,5-triazine | HCl |
| 12 | 4-amino-6-(dimethylamino)-2-(4-hydroxyphenyl)-1,2-dihydro-1,3,5-triazine | HCl |

-continued

| | Formula | Salt |
|---|---|---|
| 13 | (structure: 4,6-diamino-triazine with N(CH₃)₂ and NH₂ substituents, and 4-hydroxyphenyl group) | |
| 14 | (structure: triazine with N(CH₃)₂, NHCH₂CH₃, and gem-dimethyl) | Fumarate |
| 15 | (structure: triazine with two N(CH₃)₂ groups and gem-dimethyl) | HCl |
| 16 | (structure: triazine with N(CH₃)₂, NHCH₃, and gem-dimethyl) | HCl |
| 17 | (structure: triazine with N(CH₃)₂, pyrrolidinyl, and gem-dimethyl) | HCl |
| 18 | (structure: triazine with N(CH₃)₂, NH₂, and CH₃) | HCl |

-continued
| | Formula | Salt |
|---|---|---|
| 19 | 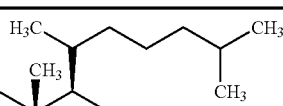 | HCl |
| 20 | 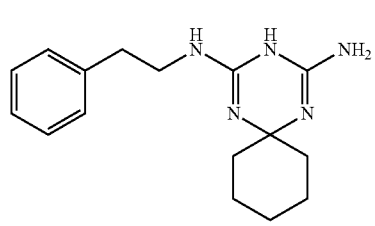 | Carbonate |
| 21 | 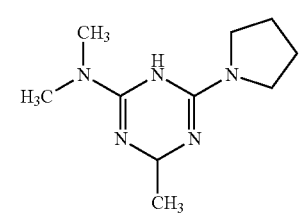 | Carbonate |
| 22 | 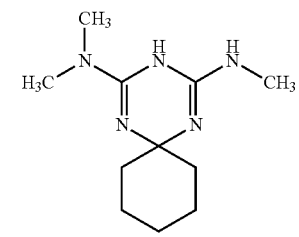 | HCl |
| 23 | 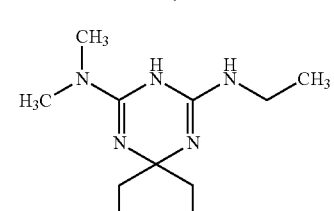 | HCl |
| 24 | 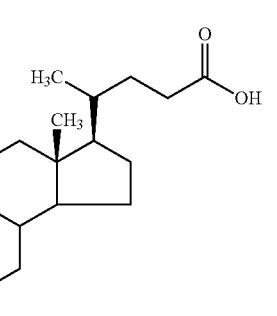 | HCl |

| | Formula | Salt |
|---|---|---|
| 25 | 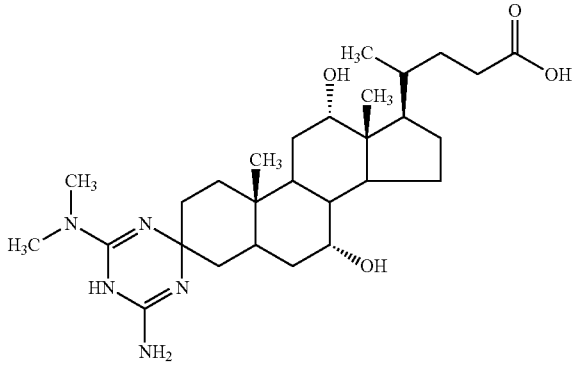 | HCl |
| 26 | 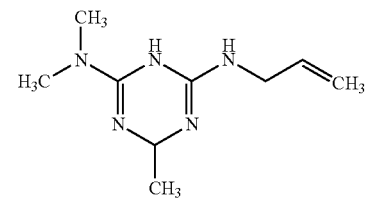 | HCl |
| 27 | 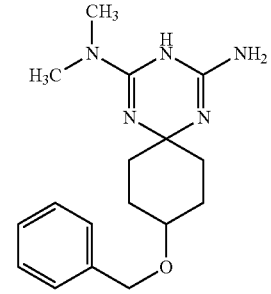 | HCl |
| 28 | 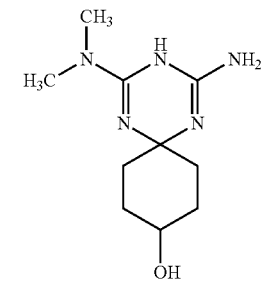 | HCl |
| 29 | 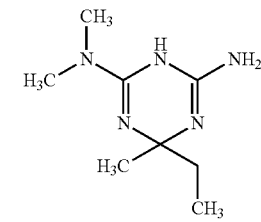 | Carbonate |

-continued

| | Formula | Salt |
|---|---|---|
| 30 | 6-membered triazine ring with N(CH₃)(H₃C), NH₂, NH substituents and two ethyl groups (CH₃CH₂) at one ring carbon | Carbonate |
| 31 | 6-membered triazine ring with N(CH₃)(H₃C), NH₂, NH substituents, spiro-fused to cyclopentane | HCl |
| 32 | 6-membered triazine ring with N(CH₃)(H₃C), NH₂, NH substituents and n-propyl group at ring carbon | Carbonate |
| 33 | 6-membered triazine ring with N(CH₃)(H₃C), NH₂, NH substituents, CH₂ at ring position | HCl |
| 34 | 6-membered triazine ring with N(CH₃)(H₃C), NH₂, NH substituents and cyclohexyl group at ring carbon | para-Toluene-sulfonate |
| 35 | 6-membered triazine ring with N(CH₃)(H₃C), NH₂, NH substituents and two methyl groups (H₃C, CH₃) at ring carbon | HCl |
| 36 | 6-membered triazine ring with N(CH₃)(H₃C), NH₂, NH substituents and CF₃ group at ring carbon | para-Toluene-sulfonate |

-continued

| | Formula | Salt |
|---|---|---|
| 37 | 6-benzyl-N2,N2-dimethyl-1,6-dihydro-1,3,5-triazine-2,4-diamine | para-Toluene-sulfonate |
| 38 | N2,N2-dimethyl-2-oxa-7,9,11-triazaspiro[5.5]undec-7(or 8)-ene-8,10-diamine analog | HCl |
| 39 | N2,N2-dimethyl-3-methyl-3,7,9,11-tetraazaspiro[5.5]undec-7-ene-8,10-diamine analog | HCl |
| 40 | 6-(furan-2-yl)-N2,N2-dimethyl-1,6-dihydro-1,3,5-triazine-2,4-diamine | HCl |
| 41 | N2,N2-dimethyl-6-(phenoxymethyl)-1,6-dihydro-1,3,5-triazine-2,4-diamine | para-Toluene-sulfonate |
| 42 | 6-tert-butyl-N2,N2-dimethyl-1,6-dihydro-1,3,5-triazine-2,4-diamine | HCl |

-continued

| | Formula | Salt |
|---|---|---|
| 43 | (structure: 2-amino-4-dimethylamino-6-isobutyl-1,3,5-triazine, dihydro) | HCl |
| 44 | (structure: 2-amino-4-dimethylamino-6-isopropyl-1,3,5-triazine, dihydro) | HCl |
| 45 | (structure: 2-amino-4-dimethylamino-6-(cyclohex-3-enyl)-1,3,5-triazine, dihydro) | para-Toluene-sulfonate | and more preferably the compound of Example 18.

The term "insulin secretion stimulator" means any agent usually used in human or veterinary therapy to stimulate insulin secretion in the case of a patient in need thereof. Sulfonylureas, glinides, glucagon receptor antagonists, incretin hormones, in particular glucagon-like-peptide-1 (GLP-1) or GLP-1 agonists, and DPP-IV inhibitors are especially preferred.

The term "glucagon receptor antagonist" in particular includes the compounds described in WO 98/04528, in particular BAY27-9955, and also those described in Bioorg. Med. Chem. Lett. 1992, 2, 915-918 and more particularly CP-99,711, those described in J. Med. Chem. 1998, 41, 5150-5157 and in particular NNC92-1687, those described in J. Biol. Chem., 1999, 274, 8694-8697 and in particular L-168, 049, and those described in U.S. Pat. No. 5,880,139, WO 99/01423, U.S. Pat. No. 5,776,954, WO 98/22109, WO 98/22108, WO 98/21957 and WO 97/16442.

The term "sulfonylureas" concerns compounds that activate the secretion of insulin by the pancreatic beta cells by transmission of a signal via sulfonylurea receptors located in the membrane. It includes (in a non-limiting manner) tolbutamide, chlorpropamide, tolazamide, acetoxamide, glycopyramide, glibenclamide/glyburide, gliclazide, 1-butyl-3-metanilyl-urea, carbutamide, glibomuride, glipizide, gliquidone, glisoxepide, gly-buthiazole, glibuzole, glyhexamide, glymidine, glypinamide, phenbut-amide, tolyl-cyclamide and glimepiride, more preferably glibenclamide/glyburide, gliclazide, glimepiride and glipizide.

The term "glinide" in particular means repaglinide.

The term "glucagon receptor agonist" in particular includes compounds, such as GLP-1(7-37), in which the terminal amide of Arg$^{36}$ is displaced with Gly to position 37 of GLP-1(7-36)NH$_2$ and also variants and analogues, such as GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1 (7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Particular preference is also given to the GLP agonist known as exendin-4, described by Greig et al. in Diabetologia, 1999, 42, 45-50.

The term "DPP-IV inhibitor" in particular includes compounds, such as, in a non-limiting manner, those described in WO 97/40832, WO 98/19998, DE 196 16 486 A1, WO 00/34241, WO 95/15309, WO 01/47514 and WO 01/52825, WO 2005/033099, WO 2005/058849 and WO 2005/075426.

The preferred compounds are 1-(2-[(5-cyanopyridin-2-yl)amino]ethyl-amino)acetyl-2(S)-cyanopyrrolidine dihydrochloride (Example 3 of WO 98/19998), (S)1-[(3-hydroxy-1-adamantyl)amino]acetyl-2-cyanopyrrolidine (Example 1 of WO 0034241), LAF-237, MK-0431, PSN-9301, BMS-477118, GW-825964, T-6666, SYR-322, PHX-1149, LC-15-0133, FE-99901, GRC-8200, KF-81364, SSR-162369, CP-867534-01 and TP-8211.

According to yet another preferred embodiment, the invention more particularly relates to pharmaceutical compositions comprising combinations chosen from:
(+)-2-amino-3,6-dihydro-4-dimethylamino-6-methyl-1,3,5-triazine hydrochloride, and glibenclamide;
(+)-2-amino-3,6-dihydro-4-dimethylamino-6-methyl-1,3,5-triazine hydrochloride, and glimepiride;

(+)-2-amino-3,6-dihydro-4-dimethylamino-6-methyl-1,3,5-triazine hydrochloride, and glipizide;

(+)-2-amino-3,6-dihydro-4-dimethylamino-6-methyl-1,3,5-triazine hydrochloride, and gliclazide.

The invention also relates to the racemic forms, tautomers, enantiomers, diastereoisomers and epimers, and mixtures thereof, and also the pharmaceutically acceptable salts and esters of the compounds of the general formula (I).

The compounds of the formula (I) according to the invention as defined above, containing a sufficiently basic function, or both, may include the corresponding pharmaceutically acceptable salts of organic or mineral acids.

For the purposes of the present invention, the term "corresponding pharmaceutically acceptable salts of organic or mineral acids" means any salt prepared from any non-toxic pharmaceutically acceptable organic or inorganic acid. Such acids include acetic acid, benzenesulfonic acid, benzoic acid, citric acid, carbonic acid, ethanesulfonic acid, fumaric acid, gluconic acid, glutamic acid, hydrobromic acid, hydrochloric acid, lactic acid, mandelic acid, malic acid, maleic acid, methanesulfonic acid, mucic acid, nitric acid, pamoic acid, pantothenic acid, phosphoric acid, succinic acid, tartaric acid and para-toluenesulfonic acid. Hydrochloric acid is advantageously used.

The invention also relates to the chiral salts of the compounds of the formula (I) used for the separation of the racemates of the compounds of the formula (I).

By way of example, the following chiral acids are used: (+)-D-di-O-benzoyltartaric acid, (−)-L-di-O-benzoyltartaric acid, (−)-L-di-O,O'-p-toluyl-L-tartaric acid, (+)-D-di-O,O'-p-toluyl-L-tartaric acid, (R)-(+)-malic acid, (S)-(−)-malic acid, (+)-camphanic acid, (−)-camphanic acid, R-(−)-1,1'-binaph-thalen-2,2'-diylhydrogenophosphonic acid, (+)-camphoric acid, (−)-camphoric acid, (S)-(+)-2-phenylpropionic acid, (R)-(+)-2-phenylpropionic acid, D-(−)-mandelic acid, L-(+)-mandelic acid, D-tartaric acid, L-tartaric acid, or a mixture of two or more thereof.

The enantiomers of the compounds according to the invention and to the process for separating them are especially described in patent application WO 2004/089917, the content of which is incorporated herein by reference.

The present patent application also relates to the polymorphic forms of the compounds, as obtained according to patent application WO 2004/089917, for instance the A1 polymorphic form of the salt (+)-2-amino-3,6-dihydro-4-dimethylamino-6-methyl-1,3,5-triazine hydrochloride.

The present invention also relates to the other polymorphic forms of the compounds, such as the H1 polymorphic form of the salt (+)-2-amino-3,6-di-hydro-4-dimethylamino-6-methyl-1,3,5-triazine hydrochloride, which can be prepared as follows:

Approximately 3 g of the A1 form of Example 18 are dissolved in 50 ml of 1 mol/l HCl at room temperature. The clear solution obtained is left to evaporate at room temperature, in an open beaker, until a solid residue crystallises.

The characterisation is performed by:
FT-IR spectroscopy:
Brüker Vector 22
2 cm$^{-1}$ spectral resolution
32 scans
KBR discs (analogous to method A AA21505)
To evaluate the intensity of the IR bands, the IR spectra were normalised by vectorisation in the spectral range 4000-400 cm$^{-1}$ as an absorption spectrum.
Preadjustment was performed:
s: A>0.05
m: 0.01<A<0.05
w: A<0.01.
FT-Raman spectroscopy:
Brüker RFS-100
excitation: 1064 nm
spectral resolution: 1 cm$^{-1}$
1000 mW
1000 scans
focalised
aluminium crucible (analogous to method RA AA21505)
To evaluate the intensity of the Raman bands, Raman spectra were normalised by vectorisation in the spectral range 3600-200 cm$^{-1}$.
Preadjustment was performed:
s: A>0.05
m: 0.01<A<0.05
w: A<0.01
Powder x-ray diffraction (XRD)
diffractometer D5000 (Brüker AXS)
radiation CuKα1 at 1.5406 Å (U=30 kV, A=40 mA)
Transmission mode
Detector in sensitive position
Primary monochromator
Angle range: 3-65 °2θ
Stage width: 0.05 °2θ
Measuring time/stage: 1.4 s
The XRD machine is set at 2θ±0.1°.
Results
A1 form:
XRD:

| No. | d [Å] | 2θ | I/Io |
| --- | --- | --- | --- |
| 1 | 5.98 | 14.8 | 85 |
| 2 | 5.26 | 16.8 | 83 |
| 3 | 4.35 | 20.4 | 30 |
| 4 | 3.57 | 24.9 | 100 |
| 5 | 3.50 | 25.4 | 53 |
| 6 | 3.36 | 26.5 | 96 |
| 7 | 3.31 | 26.9 | 52 |
| 8 | 3.04 | 29.3 | 57 |
| 9 | 2.90 | 30.8 | 30 |
| 10 | 2.74 | 32.7 | 35 |

FT-IR bands (in cm$^{-1}$):
3384+/−1.5 (m), 3199+/−1.5 (m), 3163+/−1.5 (m), 3107+/−1.5 (m), 2993+/−1.5 (m), 2983+/−1.5 (m), 1652+/−1.5 (s), 1606+/−1.5 (s), 1576+/−1.5 to (s), 1557+/−1.5 (s), 1505+/−1.5 (s), 1449+/−1.5 (m), 1427+/−1.5 (m), 1405+/−1.5 (m), 1383+/−1.5 (m), 1348+/−1.5 (m), 1306+/−1.5 (m), 1263+/−1.5 (w), 1235+/−1.5 (w), 1185+/−1.5 (w), 1096+/−1.5 (w), 1068+/−1.5 (w), 980+/−1.5 (w), 946+/−1.5 (w), 868+/−1.5 (w), 761+/−1.5 (w), 687+/−1.5 (m), 655+/−1.5 (m), 558+/−1.5 (w), 521+/−1.5 (w), 478+/−1.5 (w)

FT-Raman bands (in cm$^{-1}$):
3217+/−1.5 (w), 2994+/−1.5 (m), 2983+/−1.5 (m), 2936+/−1.5 (s), 2883+/−1.5 (m), 1645+/−1.5 (w), 1602+/−1.5 (m), 1554+/−1.5 (m), 1453+/−1.5 (m), 1428+/−1.5 (m), 1349+/−1.5 (w), 1308+/−1.5 (w), 979+/−1.5 (m), 866+/−1.5 (w), 761+/−1.5 (w), 686+/−1.5 (s), 583+/−1.5 (m), 555+/−1.5 (s), 525+/−1.5 (m), 479+/−1.5 (m), 410+/−1.5 (m), 401+/−1.5 (m), 307+/−1.5 (m)

H1 form
XRD:

| No. | d [Å] | 2θ | I/Io |
|-----|-------|------|------|
| 1 | 8.03 | 11.0 | 69 |
| 2 | 7.27 | 12.2 | 25 |
| 3 | 6.11 | 14.5 | 24 |
| 4 | 4.01 | 22.1 | 86 |
| 5 | 3.64 | 24.5 | 100 |
| 6 | 3.26 | 27.3 | 51 |
| 7 | 3.08 | 29.0 | 29 |
| 8 | 3.04 | 29.4 | 34 |
| 9 | 2.82 | 31.7 | 61 |
| 10 | 2.66 | 33.6 | 26 |

FT-IR bands (in $cm^{-1}$):
3386+/−1.5 (m), 3080+/−3 (m), 1706+/−1.5 (s), 1691+/−1.5 (s), 1634+/−1.5 (m), 1513+/−1.5 (m), 1445+/−1.5 (w), 1241+/−1.5 (w), 1079+/−1.5 (w), 989+/−1.5 (w), 940+/−1.5 (w), 861+/−1.5 (w), 823+/−1.5 (w), 675+/−1.5 (w), 603+/−1.5 (w), 573+/−1.5 (w), 549+/−1.5 (w), 527+/−1.5 (w)

The compounds of the formula (I) above also include the prodrugs of these compounds.

The term "prodrugs" means compounds which, when administered to the patient, are chemically and/or biologically converted in the live body into compounds of the formula (I).

In the present description, the terms used have, unless otherwise indicated, the following meanings:

- the term "(C1-C20)alkyl" denotes a linear or branched alkyl radical containing from 1 to 20 carbon atoms. Among the C1-C20 alkyl radicals that may especially be mentioned, in a non-limiting manner, are methyl, ethyl, propyl, isopropyl, butyl, sec-butyl, tert-butyl, pentyl, hexyl, octyl, decyl, dodecyl, hexadecyl and octadecyl radicals;
- the term "(C1-C20)alkenyl" denotes a linear or branched hydro-carbon-based radical containing one or more unsaturations in double bond form. As alkylene radicals containing from 1 to 20 carbon atoms, mention may be made, in a non-limiting manner, of ethenyl, prop-2-enyl, but-2-enyl, but-3-enyl, pent-2-enyl, pent-3-enyl and pent-4-enyl radicals;
- the term "(C1-C20)alkynyl" denotes a linear or branched hydrocarbon-based radical containing one or more unsaturations in triple bond form. As alkylene radicals containing from 1 to 20 carbon atoms, mention may be made, in a non-limiting manner, of ethynyl, prop-2-ynyl, but-2-ynyl, but-3-ynyl, pent-2-ynyl, pent-3-ynyl and pent-4-ynyl radicals;
- the term "alkoxy" refers to the term "alkyl-oxy";
- the term "halogen" refers, in a non-limiting manner, to fluorine, chlorine or bromine;
- the term "(C6-C14)aryl" refers to an aromatic group containing is from 6 to 14 carbon atoms with at least one of the rings having a system of conjugated pi electrons, and including biaryls, which may be optionally substituted. Mention will be made in particular of biphenyl, phenyl, naphthyl, anthryl and phenanthryl radicals;
- the term "hetero(C6-C14)aryl" refers to a 6-14-membered aromatic heterocycle containing 1-4 heteroatoms, the other atoms being carbon atoms. Among the heteroatoms, mention will be made in particular of oxygen, sulfur and nitrogen. Among the heteroaryl radicals, mention will be made more particularly of furyl, thienyl, pyridyl, pyrrolyl, pyrimidyl, pyrazinyl, oxazolyl, oxadiazolyl, isoxazolyl, quinolyl and thiazolyl radicals;
- the term "(C3-C8)cycloalkyl" refers to a saturated hydrocarbon-based ring and includes monocyclic, bicyclic and polycyclic radicals containing from 3 to 8 carbon atoms. Mention will be made, in a non-limiting manner, of cyclopropyl and cyclobutyl radicals;
- the term "(C6-C14)aryl(C1-C20)alkyl" refers to the corresponding-alkylaryl groups. Mention will be made in particular of benzyl and phenethyl groups.

It will be appreciated that the compounds that are useful according to the present invention may contain asymmetric centres. These asymmetric centres may be, independently, in R or S configuration. It will be clear to a person skilled in the art that certain compounds that are useful according to the invention may also exhibit geometrical isomerism. It should be understood that the present invention includes individual geometrical isomers and stereoisomers and mixtures thereof, including racemic mixtures, of compounds of the formula (I) above. Isomers of this type can be separated from mixtures thereof by application or adaptation of known processes, for example chromatography techniques or recrystallisation techniques, or they are prepared separately from suitable isomers of their to intermediates.

For the purposes of this text, it is understood that the tautomeric forms are included in the mention of a given group, for example thio/mercapto or oxo/hydroxy.

The pharmaceutical compositions according to the present invention are useful in the treatment of pathologies associated with insulin resistance syndrome (syndrome X).

Insulin resistance is characterised by a reduction in the action of insulin (cf. Presse Médicale, 1997, 26 (No. 14), 671-677) and is involved in a large number of pathological conditions, such as diabetes and more particularly non-insulin-dependent diabetes (type II diabetes or NIDDM), dyslipidaemia, obesity and arterial hypertension, and also certain microvascular and macrovascular complications, for instance atherosclerosis, retinopathy and neuropathy.

In this respect, reference will be made, for example, to Diabetes, vol. 37, 1988, 1595-1607; Journal of Diabetes and its Complications, 1998, 12, 110-119 or Horm. Res., 1992, 38, 28-32.

The aim of the present invention is to propose a pharmaceutical composition for significantly improving the condition of diabetics and more particularly for optimising the use of glucose.

The pharmaceutical compositions of the invention especially have hypoglycaemiant activity.

The compounds of the formula (I) are therefore useful in the treatment of pathologies associated with hyperglycaemia.

The pharmaceutical composition comprising the triazine compound of the formula (I) in combination with an insulin secretion stimulator can be prepared by mixing together the various active principles, either all together or independently with a physiologically acceptable support, an excipient, a binder, a diluent, etc. It is then administered orally or non-orally, for instance via the parenteral, intravenous, cutaneous, nasal or rectal route. If the active principles are formulated independently, the corresponding formulations may be mixed together extemporaneously using a diluent and are then administered or may be administered independently to of each other, either successively or sequentially.

The pharmaceutical compositions of the invention includes formulations such as granules, powders, tablets, gel capsules, syrups, emulsions and suspensions, and also forms used for non-oral administration, for instance injections, sprays or suppositories.

The pharmaceutical forms can be prepared via the known conventional techniques.

The preparation of an orally administered solid pharmaceutical form will be performed by the following process: an excipient (for example lactose, sucrose, starch, mannitol, etc.), a disintegrant (for example calcium carbonate, calcium carboxymethylcellulose, alginic acid, sodium carboxy-methylcellulose, colloidal silicon dioxide, sodium croscarmellose, Crospovidone, guar gum, magnesium aluminium silicate, microcrystalline cellulose, cellulose powder, pregelatinised starch, sodium alginate, starch glycolate, etc.), a binder (for example alpha-starch, gum arabic, carboxy-methylcellulose, polyvinylpyrrolidone, hydroxypropylcellulose, alginic acid, carbomer, dextrin, ethylcellulose, sodium alginate, maltodextrin, liquid glucose, magnesium aluminium silicate, hydroxyethylcellulose, methylcellulose, guar gum, etc.) and a lubricant (for example talc, magnesium stearate, polyethylene 6000, etc.) are, for example, added to the active principle(s) and the mixture obtained is then tabletted. If necessary, the tablet can be coated via the known techniques, in order to mask the taste (for example with cocoa powder, mint, borneol, cinnamon powder, etc.) or to allow enteric dissolution or sustained release of the active principles. The coating products that can be used are, for example, ethylcellulose, hydroxymethylcellulose, polyoxyethylene glycol, cellulose acetophthalate, hydroxypropylmethylcellulose phthalate and Eudragit® (methacrylic acid-acrylic acid copolymer), Opadry® (hydroxypropylmethylcellulose+macrogol+titanium oxide+lactose monohydrate). Pharmaceutically acceptable colorants may be added (for example yellow iron oxide, red iron oxide, quinoline yellow lake, etc.). Pharmaceutical forms such as tablets, powders, sachets and gel capsules can be used for an oral administration.

The liquid pharmaceutical forms for oral administration include solutions, suspensions and emulsions. The aqueous solutions can be obtained by dissolving the active principles in water, followed by addition of flavourings, colorants, stabilisers and thickener, if necessary. In order to improve the solubility, it is possible to add ethanol, propylene glycol or other pharmaceutically acceptable non-aqueous solvents. The aqueous is suspensions for oral use can be obtained by dispersing the finely divided active principles in water with a viscous product, such as natural or synthetic gums, resins, methylcellulose or sodium carboxymethylcellulose.

The pharmaceutical forms for injection can be obtained, for example, by the following process. The active principle(s) is (are) dissolved, suspended or emulsified either in an aqueous medium (for example distilled water, physiological saline, Ringer's solution, etc.) or in an oily medium (for example a plant oil, such as olive oil, sesameseed oil, cottonseed oil, corn oil, etc., or propylene glycol), with a dispersant (for example Tween 80, HCO 60 (Nikko Chemicals), polyethylene glycol, carboxy-methylcellulose, sodium alginate, etc.), a preserving agent (for example methyl p-hydroxybenzoate, propyl p-hydroxybenzoate, benzyl alcohol, chlorobutanol, phenol, etc.), an isotonicity agent (for example sodium chloride, glycerol, sorbitol, glucose, etc.) and also other additives, such as, if desired, a solubilising agent (for example sodium salicylate, sodium acetate, etc.) or a stabiliser (for example human serum albumin).

A pharmaceutical form for external use can be obtained from a solid, semi-solid or liquid composition containing the active principle(s). For example, to obtain a solid form, the active principle(s) is (are) treated, alone or as mixtures with excipients (for example lactose, mannitol, starch, microcrystalline cellulose, sucrose, etc.) and a thickener (for example natural gums, cellulose derivatives, acrylic polymers, etc.) so as to convert them into powder. The liquid pharmaceutical compositions are prepared in substantially the same way as the forms for injection, as indicated previously. The semi-solid pharmaceutical forms are preferably in the form of aqueous or oily gels or in the form of a pomade. These compositions may optionally contain a pH regulator (for example carbonic acid, phosphoric acid, citric acid, hydrochloric acid, sodium hydroxide, etc.) and a preserving agent (for example p-hydroxybenzoic acid esters, chlorobutanol, benzalkonium chloride, etc.) and also other additives.

The relative proportion of the constituents of the pharmaceutical compositions of the present invention takes into account the recommended dosages of the respective active principles. The ratios of the respective amounts of the insulin secretion stimulator and of the compound of the formula (I) thus vary in consequence.

The weight ratio of the insulin secretion stimulator to the compound of the formula (I) preferably ranges between 1/1000 and particularly from 4/100 and especially from 1/500 to 4/100 or more preferably from 1/300 to 4/100. The dosages will depend on those usually used for the active principles. Thus, for the insulin secretion stimulator, the dosages are between 1 and 6 mg/day for glimepiride, from 1.5 to 15 mg/day for glibenclamide, from 30 to 120 mg/day for gliclazide and from 2.5 to 20 mg/day for glipizide.

For the compound of the formula (I), the daily dosages range from 200 mg to 2000 mg. The preferred frequency of administration of the compounds of the invention is between one and two administrations per day. In cases where the doses of compounds of the formula (I) require more than one daily administration, the amounts of insulin secretion stimulator and the insulin secretion stimulator/compound of the formula (I) ratio will be adjusted in consequence.

The aim of the present invention is also to propose a method of treatment via co-administration of an effective amount of a compound of the formula (I) and of an insulin secretion stimulator, and also kits for allowing this co-administration.

The present invention also relates to kits that are suitable for the treatment by the methods described above. These kits comprise a composition containing the compound of the formula (I) in the dosages indicated above and a second composition containing the insulin secretion stimulator in the dosages indicated above, for a simultaneous, separate or sequential administration, in effective amounts according to the invention.

The term "co-administration" means the simultaneous, separate or to sequential administration of one or more compounds to the same patient, over a period that may be up to 2 hours or even up to 12 hours. For example, the term co-administration includes:

(1) a simultaneous administration of the two compounds,
(2) an administration of the first, followed 2 hours later by the administration of the second compound,
(3) an administration of the first, followed 12 hours later by the administration of the second compound.

The examples below of compositions according to the invention are given as non-limiting illustrations.

EXAMPLES

The amounts are expressed on a weight basis.

Formulation Example 1

(+)-2-amino-3,6-dihydro-4-dimethylamino-6-methyl-1,3,5-triazine hydrochloride: 1000 mg
glibenclamide: 5 mg
microcrystalline cellulose: 113 mg croscarmellose: 28 mg
polyvinylpyrrolidone: 40 mg
magnesium stearate: 14 mg
Opadry: 24 mg Formulation Example 2

(+)-2-amino-3,6-dihydro-4-dimethylamino-6-methyl-1,3,5-triazine hydrochloride: 1000 mg
glibenclamide: 2.5 mg
microcrystalline cellulose: 115.5 mg
croscarmellose: 28 mg
polyvinylpyrrolidone: 40 mg
magnesium stearate: 9 mg
Opadry®: 24 mg Formulation Example 3

(+)-2-amino-3,6-dihydro-4-dimethylamino-6-methyl-1,3,5-triazine hydrochloride: 750 mg
glibenclamide: 5 mg
microcrystalline cellulose: 89 mg
croscarmellose: 21 mg
polyvinylpyrrolidone: 30 mg
magnesium stearate: 10.5 mg
Opadry®: 18 mg Formulation Example 4

(+)-2-amino-3,6-dihydro-4-dimethylamino-6-methyl-1,3,5-triazine hydrochloride: 1000 mg
gliclazide: 30 mg
microcrystalline cellulose: 150 mg
croscarmellose: 24 mg
polyvinylpyrrolidone: 44 mg
magnesium stearate: 8 mg
Eudragit®: 24 mg Formulation Example 5

(+)-2-amino-3,6-dihydro-4-dimethylamino-6-methyl-1,3,5-triazine hydrochloride: 1000 mg
glimepiride: 1 mg
Silicon dioxide: 4 mg
croscarmellose: 25 mg
polyvinylpyrrolidone: 40 mg
magnesium stearate: 8 mg
Opadry®: 10 mg Biological Test: Modulation of Glucose Levels with the Combinations of the Invention with Insulin Secretion Stimulators The capacity of the compounds of the invention in combination with insulin secretion stimulator antidiabetic compounds to modify the blood is glucose levels is evaluated in vivo in diabetic GK rats.

Alone or in combination, the antidiabetic agents are administered twice a day (bid) to the GK rats for 4 days. The oral glucose tolerance test (OGTT) is performed after the last day of treatment.

OGTT is performed in the morning after 3 hours of fasting by oral administration of a glucose charge of 2 g/kg of body mass. The blood samples are collected from the tail vein at 0; 10; 20; 30; 45; 60; 90 and 120 minutes to determine the glucose levels.

The invention claimed is:

1. A pharmaceutical composition comprising, as active principle:
   i) an insulin secretion stimulator that is a glucagon receptor antagonist, an incretin hormone, DPP-IV inhibitor, a sulfonylurea or a glinide, and, 2-amino-3,6-dihydro-4-dimethylamino-6-methyl-1,3,5-triazine, or a tautomer, or a pharmaceutically acceptable salt thereof and one or more pharmaceutically acceptable excipients.

2. The pharmaceutical composition according to claim 1, wherein 2-amino-3,6-dihydro-4-dimethylamino-6-methyl-1,3,5-triazine is (+)-2-amino-3,6-dihydro-4-dimethylamino-6-methyl-1,3,5-triazine, or a tautomer or pharmaceutically acceptable salt thereof.

3. The pharmaceutical composition according to claim 1, wherein 2-amino-3,6-dihydro-4-dimethylamino-6-methyl-1,3,5-triazine is (−)-2-amino-3,6-dihydro-4-dimethylamino-6-methyl-1,3,5-triazine, or a tautomer or pharmaceutically acceptable salt thereof.

4. The pharmaceutical composition according to claim 1, wherein 2-amino-3,6-dihydro-4-dimethylamino-6-methyl-1,3,5-triazine is in the form of a hydrochloride.

5. The pharmaceutical composition according to claim 1, containing between 1 mg and 120 mg of insulin secretion stimulator.

6. The pharmaceutical composition according to claim 1, containing between 200 mg and 2000 mg of 2-amino-3,6-dihydro-4-dimethylamino-6-methyl-1,3,5-triazine.

7. The pharmaceutical composition according to claim 1, having a weight ratio of insulin secretion stimulator to 2-amino-3,6-dihydro-4-dimethylamino-6-methyl-1,3,5-triazine of between 1/1000 and 1/100.

8. The pharmaceutical composition according to claim 1, having a weight ratio of an insulin secretion stimulator to 2-amino-3,6-dihydro-4-dimethylamino-6-methyl-1,3,5-triazine of between 1/300 and 1/100.

9. The pharmaceutical composition according to claim 1, wherein the sulfonylurea is tolbutamide, chlorpropamide, tolazamide, acetoxamide, glycopyramide, glibenclamide/glyburide, gliclazide, 1-butyl-3-metanilylurea, carbutamide, glibomuride, glipizide, gliquidone, glisoxepide, glybuthiazole, glibuzole, glyhexamide, glymidine, glypinamide, phenbutamide, tolylcyclamide or glimepiride.

10. The pharmaceutical composition according to claim 1, wherein the sulfonylurea is glibenclamide, gliclazide, glimepiride or glipizide.

11. The pharmaceutical composition according to claim 1, wherein the insulin secretion stimulator is glibenclamide and 2-amino-3,6-dihydro-4-dimethylamino-6-methyl-1,3,5-triazine is (+)-2-amino-3,6-dihydro-4-dimethylamino-6-methyl-1,3,5-triazine, optionally in the form of a hydrochloride.

12. The pharmaceutical composition according to claim 1, wherein the insulin secretion stimulator is gliclazide and 2-amino-3,6-dihydro-4-dimethylamino-6-methyl-1,3,5-triazine is (+)-2-amino-3,6-dihydro-4-dimethylamino-6-methyl-1,3,5-triazine, optionally in the form of a hydrochloride.

13. The pharmaceutical composition according to claim 1, wherein the insulin secretion stimulator is glipizide and 2-amino-3,6-dihydro-4-dimethylamino-6-methyl-1,3,5-triazine is (+)-2-amino-3,6-dihydro-4-dimethylamino-6-methyl-1,3,5-triazine, optionally in the form of a hydrochloride.

14. The pharmaceutical composition according to claim 1, wherein the insulin secretion stimulator is glimepiride and 2-amino-3,6-dihydro-4-dimethylamino-6-methyl-1,3,5-triazine is (+)-2-amino-3,6-dihydro-4-dimethylamino-6-methyl-1,3,5-triazine, optionally in the form of a hydrochloride.

15. The pharmaceutical composition according to claim 1, which is suitable for oral administration, in which the pharmaceutical composition is a powder, a coated tablet, a gel capsule, a sachet, a solution, a suspension or an emulsion.

16. A method for the treatment of diabetes, comprising administering to a patient a composition as defined in claim 1.

17. A method according to claim 16, wherein said method is for the treatment of a non-insulin-dependent diabetes.

18. A method for the treatment of insulin resistance syndrome in a patient with dyslipidaemia, obesity, arterial hypertension, or microvascular or macrovascular complications, comprising administering to said patient a composition as defined in claim 1.

19. The method according to claim 16, wherein the insulin secretion stimulator is glibenclamide and 2-amino-3,6-dihydro-4-dimethylamino-6-methyl-1,3,5-triazine is (+)-2-amino-3,6-dihydro-4-dimethylamino-6-methyl-1,3,5-triazine, optionally in the form of a hydrochloride.

20. The method according to claim 16, wherein the administration of 2-amino-3,6-dihydro-4-dimethylamino-6-methyl-1,3,5-triazine and that of the insulin secretion stimulator are simultaneous, separate or sequential.

21. The method according to claim 18, wherein the patient has atherosclerosis, retinopathy, nephropathy or neuropathy.

22. The pharmaceutical composition according to claim 1, wherein the insulin secretion stimulator is a glucagon receptor antagonist.

23. The pharmaceutical composition according to claim 1, wherein the insulin secretion stimulator is an incretin hormone.

24. The pharmaceutical composition according to claim 1, wherein the insulin secretion stimulator is a DPP-IV inhibitor.

25. The pharmaceutical composition according to claim 1, wherein the insulin secretion stimulator is a glinide.

26. The pharmaceutical composition according to claim 1, wherein the insulin secretion stimulator is a sulfonylurea.

* * * * *

UNITED STATES PATENT AND TRADEMARK OFFICE
CERTIFICATE OF CORRECTION

PATENT NO. : 8,227,465 B2  
APPLICATION NO. : 12/160637  
DATED : July 24, 2012  
INVENTOR(S) : Gerard Moinet, Daniel Cravo and Didier Mesangeau Page 1 of 1

It is certified that error appears in the above-identified patent and that said Letters Patent is hereby corrected as shown below:

Column 20,  
Line 50, "WO 98/|19998" should read --WO 98/19998--.  
Line 51, "WO 01/|47514" should read --WO 01/47514--.  
Line 55, "WO 98/|19998)" should read --WO 98/19998)--.

Column 23,  
Lines 52-53, "containing is from" should read --containing from--.

Column 26,  
Line 44, "or to sequential" should read --or sequential--.

Signed and Sealed this  
Ninth Day of April, 2013

Teresa Stanek Rea  
*Acting Director of the United States Patent and Trademark Office*